United States Patent
Antebi et al.

(10) Patent No.: US 9,420,797 B2
(45) Date of Patent: *Aug. 23, 2016

(54) METHOD FOR PREPARING BIOCIDAL AQUEOUS COMPOSITIONS

(71) Applicant: BROMINE COMPOUNDS LTD., Beer Sheva (IL)

(72) Inventors: Shlomo Antebi, Haifa (IL); David Feldman, Haifa (IL); Chen Zolkov, Kiryat Tivon (IL)

(73) Assignee: Bromine Compounds Ltd., Beer Sheva (IL)

( * ) Notice: Subject to any disclaimer, the term of this patent is extended or adjusted under 35 U.S.C. 154(b) by 72 days.

This patent is subject to a terminal disclaimer.

(21) Appl. No.: 14/385,216

(22) PCT Filed: Mar. 19, 2013

(86) PCT No.: PCT/IL2013/050259
§ 371 (c)(1),
(2) Date: Sep. 15, 2014

(87) PCT Pub. No.: WO2013/140402
PCT Pub. Date: Sep. 26, 2013

(65) Prior Publication Data
US 2015/0044300 A1    Feb. 12, 2015

Related U.S. Application Data

(60) Provisional application No. 61/613,603, filed on Mar. 21, 2012, provisional application No. 61/616,661, filed on Mar. 28, 2012.

(51) Int. Cl.
*A61L 11/00* (2006.01)
*A01N 59/00* (2006.01)
*C02F 1/76* (2006.01)
*A01N 25/02* (2006.01)
*A01N 47/28* (2006.01)

(52) U.S. Cl.
CPC ............... *A01N 59/00* (2013.01); *A01N 25/02* (2013.01); *A01N 47/28* (2013.01); *C02F 1/76* (2013.01); *C02F 2209/06* (2013.01)

(58) Field of Classification Search
None
See application file for complete search history.

(56) References Cited

U.S. PATENT DOCUMENTS

| 9,133,109 B2* | 9/2015 | Antebi | A01N 47/28 |
| 2013/0178532 A1* | 7/2013 | Antebi | A01N 47/28 514/588 |

FOREIGN PATENT DOCUMENTS

| WO | 03073848 A1 | 9/2003 |
| WO | 2007089539 A2 | 8/2007 |
| WO | 2007089539 A3 | 8/2007 |
| WO | 2010143183 A2 | 12/2010 |
| WO | 2010151726 A1 | 12/2010 |
| WO | 2012038954 A2 | 3/2012 |

OTHER PUBLICATIONS

Communication and Supplementary European Search Report from a counterpart foreign application—PCT/IL2013050259—mailed Jul. 3, 2015; 22 pages.
Blatchley E. R. et al.: Environmetal Sci and Technol. 44 (2010) 8529-34; XP55085514.
Nakagawara S. et al.: Analytical Chemistry, Japan Society for Analytical Chemistry, Tokyo JP vol. 14, No. 4 (1998) 691-8; XP002974725.
Seymur S. Block editor: Disinfection, Sterilization, and Preservation Lippincott, Philadelphia, PA, pp. 135-140; XP002513675.
Notification Concerning transmittal of international preliminary report on patentability from a counterpart foreign application—PCT/IL2013050259—mailed Oct. 2, 2014—10 pages.

* cited by examiner

*Primary Examiner* — Susan Tran
(74) *Attorney, Agent, or Firm* — Roach Brown McCarthy & Gruber, P.C.; Kevin D. McCarthy

(57) ABSTRACT

An aqueous biocidal composition comprising a mixture of hydrochloric acid (HCl), urea, and sodium hypochlorite (NaOCl) at acidic pH, a method for manufacturing the composition and a biocidal technology for treating industrial water.

25 Claims, No Drawings

METHOD FOR PREPARING BIOCIDAL AQUEOUS COMPOSITIONS

FIELD OF THE INVENTION

The present invention relates to biocidal and antifouling aqueous solutions combining biocidal effects of low pH and active chlorine.

BACKGROUND OF THE INVENTION

An undesired accumulation of organisms or organic residues in liquid volumes or on wet surfaces is controlled by a variety of methods, including mechanical treatments, modifying water concentration, applying organic and inorganic biocidal materials, changing temperature, etc. There is perpetual demand for new methods, because known methods are not always applicable, and new situations incessantly appear, as well as new or resistant contaminants. Active chlorine is popular, frequently in the form of hypochlorite alkali solutions. However, alkali solutions are not always desirable. It is therefore an object of the invention to provide a method for manufacturing an acidic biocidal composition based on active chlorine.

It is another object of the invention to provide means for achieving very high biocidal effect on the site of need, eventually by combining cheap, safe, and easily available precursor components in a high concentration.

Other objects and advantages of present invention will appear as description proceeds.

SUMMARY OF THE INVENTION

The invention provides a method for manufacturing a biocidal and antifouling composition in an aqueous mixture, comprising the steps of i) providing an aqueous solution A containing HCl at a concentration of between 5 wt % and 15 wt %, and urea at a weight ratio of urea/HCl of from 0.7 to 7; ii) providing an aqueous solution B comprising NaOCl; and iii) combining said aqueous solutions A and B; wherein said solutions A and B are combined, optionally with an amount of additional water, in such a ratio of volumes as to provide a pH lower than 6.0. Said pH is usually lower than 5, depending on the dilution of solutions A and B in the treated waters, possibly lower than 4. In concentrated mixtures, usable as stock solutions, the pH may be 3 or lower, possibly 2.5 or lower such as 2.0 or lower.

The invention relates to a method for manufacturing a biocidal composition in an aqueous mixture, the method comprising the steps of i) providing aqueous solution A containing HCl at a concentration of between 5 wt % and 15 wt %, and urea at a weight ratio of urea/HCl of from 0.7 to 7; ii) providing aqueous solution B containing sodium hypochlorite (NaOCl) in an amount corresponding to a weight ratio of NaOCl to said HCl in said solution A of from 1.0 to 2.0; and iii) providing said aqueous mixture by combining said aqueous solutions A and B, the solutions A and B being preferably in equal volumes, with an amount of additional water; wherein said solutions A and B create an acidic pH in said aqueous mixture and active chlorine in a concentration of less than 25 wt % (as $Cl_2$). Biocidal or antifouling compositions manufactured according to the invention usually contain active chlorine of up to 20 wt %, such as from 1 wt % to 20 wt %, or from 0.1 wt % to 12.5 wt %, in some applications from 0.1 wt % to 1 wt %, and in other applications 0.1 ppm or more, such as 1000 ppm or less, or 300-1000 ppm, or 20-1000 ppm, or 20-300 ppm, or 1-20 ppm, or 1-10 ppm, or 0.1-10 ppm. In the first aspect of the invention, said amount of additional water is not higher than the quantity of solutions A and B, and said aqueous mixture contains very high concentration of the biocidal species, reaching the highest value in a limiting case when said amount of additional water approaches zero. In one embodiment of the first aspect, said amount is a predetermined amount of water adjusting the concentration of the biocidal composition to a desired value, resulting in a mixture ready as a concentrated stock, for example having active chlorine between 1 and 20 wt %, for anti-fouling treatment in additional aqueous mixtures into which the stock is admixed. In the second aspect of the invention, said amount of additional water in step iii) is higher than the quantity of solutions A and B, and said aqueous mixture contains biocidal species in various dilutions sufficient to prevent or inhibit or eliminate biofouling in the mixture and on the surfaces in contact with the mixture. In one embodiment of the second aspect, said amount of additional water comprises an excess of water in a container or stream to be treated, resulting in an aqueous mixture having an acidic pH and active chlorine down to 20 ppm or less, for example down to between 0.1 and 10 ppm.

The invention provides a method for manufacturing an a biocidal composition in an aqueous mixture, comprising steps of i) admixing solution A into said aqueous mixture, wherein said solution A contains HCl at a concentration of between 5 wt % and 15 wt % and urea at a weight ratio of urea/HCl of from 0.7 to 7; and ii) admixing solution B into said aqueous mixture, wherein said solution B contains an oxidizer, preferably sodium hypochlorite (NaOCl) in an amount corresponding to a weight ratio of NaOCl to said HCl in said solution A of from 1.0 to 2.0; thereby creating a pH of 3.0 or less in said aqueous mixture and active chlorine at a concentration of less than 25 wt % (as $Cl_2$). In some embodiments, said steps i) and ii) may comprise adding additional water to solutions A and/or B before their admixing to said aqueous mixture. The additions can be done consecutively or in parallel; the additions can be performed by injecting or pumping or pouring the predetermined volumes into containers, tanks, or circuits comprising waters to be treated. In one embodiment of the invention, one of the solutions is injected to a water system, and only after dispersing said solution and reaching essentially homogeneity, the other solution is injected to produce the biocidal composition comprising biocidal species in concentrations sufficient for disinfection and to inhibit or eliminate biofouling. The injections of the solutions may be performed simultaneously or in any order, possibly repeatedly. Said hydrochloric acid may be admixed into water or into an aqueous mixture of urea, wherein said hydrochloric acid is added as a gas or as a water solution. Said urea may be added as a solid or as a water solution. Said NaOCl may be added as an alkali water solution. In one embodiment of the invention, said urea/HCl ratio is between 1.0 and 6.0, preferably between 1.5 and 6.5. In a preferred embodiment of the invention, the method comprises i) admixing solution A into an aqueous mixture, wherein said solution A contains HCl between 10 wt % and 15 wt % and urea at a weight ratio of urea/HCl of between 0.7 and 7, thereby obtaining a solution having a pH of 0.0 or less; and ii) admixing solution B into said aqueous mixture or contacting solution B with said solution A in said mixture, wherein said solution B contains sodium hypochlorite (NaOCl) in an amount corresponding to a weight ratio of NaOCl to HCl in said solution A of between 1.0 and 2.0; thereby creating active chlorine of less than 12.5 wt % (as $Cl_2$) and a pH of 3.0 or less.

Preferably the method comprises combining at least two liquid streams, one of which comprises said solution A and the other said solution B. In another embodiment of the invention, the method comprises combining at least two liquid streams, one of which comprises aqueous solution of HCl and urea, and the other aqueous solution of NaOCl. In the method according to the invention, the combined solutions A and B provide an acidic pH; the pH may be 3 or less in concentrated mixtures, also usable as stock solutions, whereas in the treated containers or streams the pH may be 4 or less, or eventually 5 or less, or at very low concentrations of active halogen the pH may be 6 or less. In some embodiments of the invention, the stock solutions A and B will be employed by a skilled chemist in such a way, that preliminary mixing tests will decide the mixing ratios in order to provide the required pH.

The invention relates to an aqueous biocidal composition comprising a mixture of hydrochloric acid (HCl), urea, and sodium hypochlorite (NaOCl), wherein said HCl is added as a solution of a concentration of between 5 wt % and 15 wt %, urea is added as a solution having a weight ratio of urea/HCl of between 0.7 and 7; and NaOCl is added to an amount corresponding to a weight ratio of NaOCl/HCl of between 1.0 and 2.0. Said biocidal composition comprises active chlorine at a concentration of less than 25 wt %. Said biocidal composition preferably has a pH of less than 6, such as less than 5, for example less than 4.0 or less than 3.0. The biocidal composition acts synergistically against biofouling agents by means of active halogen and high acidity, having an active chlorine less than 12.5 wt % and a pH less than 6. Said biocidal composition disinfects and neutralizes biofouling agents by means of active halogen in an acidic pH, wherein said halogen is active chlorine at a concentration higher than 0.1 ppm, for example between 1 and 20 ppm.

The invention provides a method for manufacturing a biocidal and antifouling composition in an aqueous mixture, comprising the steps of i) providing an aqueous solution A containing HCl at a concentration of between 5 wt % and 15 wt %, and urea at a weight ratio of urea/HCl of from 0.7 to 7; ii) providing an aqueous solution B comprising NaOCl; and iii) combining said aqueous solutions A and B; wherein said solutions A and B are combined, optionally with an amount of additional water, in such a ratio of volumes as to provide a pH lower than 6.0, wherein said aqueous mixture comprises industrial waters selected from cooling water, production water, water for agricultural use, water in paper mill process, effluent water, or waste water. The invention is directed to a biocidal technology for treating industrial waters, production aqueous streams, cooling towers, waters in pulp and paper industry, effluent waters, irrigation systems and agricultural equipments, or meat and poultry products, comprising two aqueous solutions, A and B, the former containing HCl at a concentration of between 5 wt % and 15 wt % and urea at a weight ratio of urea/HCl of from 0.7 to about 7, and the latter containing sodium hypochlorite (NaOCl) in an amount corresponding to a weight ratio of NaOCl to said HCl in said solution A of from about 1.0 to about 2.0. Said solutions may be combined to produce a biocidal composition having an acidic pH and containing active halogen of less than 25 wt %. Said solutions may be combined before or after contacting said industrial waters. Said solutions may be diluted with water before being combined.

DETAILED DESCRIPTION OF THE INVENTION

It has now been found that biologically contaminated waters can be very efficiently treated by combined effects of active halogen and acidic pH, comprising admixing concentrated components, or a mixture thereof, into the treated water, the components being selected from urea, acid such as HCl, urea acidic salt, and an oxidizer, where the biocidal species are formed before or after contacting said components with said contaminated waters, for example in situ. For example, a commercial oxidizer, such as hypochlorite, in the presence of urea and HCl may provide the biocidal effects.

The method and the biocidal composition of the invention provide persistent killing effect and they prevent the development of biofilms even after long time periods, as experimentally demonstrated.

In a preferred embodiment, the method of the invention comprises contacting the treated volume or surface with at least two liquid streams, one of which comprises an aqueous solution of HCl with urea and the other a commercial oxidizer, such as alkali hypochlorite.

The method enables to handle even the most arduous biofouling agents, while avoiding the direct use of elemental halogens, or the use of alkali solutions when desired. Simple stable stock solutions may be combined before the desired treatment, comprising, for example, stock solution of HCl mixed with urea, and stock solution of concentrated oxidizer such as NaOCl.

It is believed that the enhanced effects of the composition according to the invention have several reasons. Urea is believed to effectively mediate the oxidizing effects by binding at least a part of the present active halogen in the form of chlorourea. Unreacted HCl renders the composition acidic, which assists in neutralizing a part of the biofouling and fouling agents and enhances the biological activity of the obtained biocidal species. The low pH may enhance the biocidal activity and combine with the oxidizing effects of the active halogen.

In some embodiments, the biocidal activity of an acidic composition comprising urea and active chlorine according to the invention eliminates living organisms which otherwise cause biofouling within less than 24 hours. A concentrated precursor solution containing urea and hydrochloric acid may be employed, comprising urea hydrochloride and eventual excess of either urea or hydrochloric acid.

The invention provides a method of treating volumes or surfaces to eliminate or prevent biofouling, while employing concentrated stock solutions of stable precursors that are able to produce biocide species on site from relatively smaller volumes. Compared with many known methods which use unstable or dangerous or environmentally damaging chemicals, the method according to the invention comprises safe transport of concentrated solutions, which are, moreover, stable on prolonged storage. The method according to the invention enables to make anti-biofouling activities more efficient at lower cost.

The invention is directed to a process of preventing or eliminating biofouling in industrial waters, like cooling towers, pulp and paper industry, production aqueous streams, effluent treatment or agricultural applications, and the like. The waters may be treated in static containers or in dynamic streams. In one embodiment, the stream comprises production circuits in paper mill, for example comprising pulp slurry. The treatment may be applied in an effluent to be released from an industrial process. Generally, the method and the composition of the invention are useful in treating waters which are intermediate or terminal streams in industrial and agricultural processes. The aqueous mixtures to be treated according to the invention may, for example, comprise industrial waters selected from cooling water, water for agricultural use, water in paper mill process, or waste water.

The instant method enables to lower the volumes of reagents employed in anti-biofouling treatments. Both the volumes of reagents injected into the treated waters and the volumes of stock solutions are reduced, simplifying storage, transport and handling.

The invention relates to a method for preventing or eliminating biofouling in an aqueous mixture, the mixture comprising industrial or agricultural water in a container or in a circuit, comprising steps of i) admixing solution A into said aqueous mixture, wherein said solution A contains HCl at a concentration of between 5 wt % and 15 wt % and urea at a weight ratio of urea/HCl of from 0.7 to 7; and ii) admixing solution B into said aqueous mixture, wherein said solution B contains sodium hypochlorite (NaOCl) in an amount corresponding to a weight ratio of NaOCl to said HCl in said solution A of from 1.0 to 2.0; thereby creating active chlorine in said mixture. The mixture may comprise a water bulk or a water stream, and said solutions A and B may be admixed in any order. In one embodiment of the invention, one of the solutions is injected to a water system, and only after dispersing said solution and reaching essentially homogeneity, the other solution is injected to produce the biocidal composition comprising biocidal species in concentrations sufficient to inhibit or eliminate biofouling. The injections of the solutions may be performed simultaneously or in any order, possibly repeatedly.

The invention is directed to a biocidal technology comprising two aqueous solutions, A and B, the former containing HCl at a concentration of between 5 wt % and 15 wt % and urea at a weight ratio of urea/HCl of from 0.7 to about 7, and the latter containing sodium hypochlorite (NaOCl) in an amount corresponding to a weight ratio of NaOCl to said HCl in said solution A of from about 1.0 to about 2.0; wherein said solutions are combined to produce a biocidal composition having an acidic pH and containing active halogen of less than 25 wt %. Said solutions may be combined before or after contacting said industrial waters. Said solutions may be optionally diluted with water before being combined.

The invention relates to a method for making a biocidal composition for treating industrial waters, comprising i) providing aqueous solution A containing HCl at a concentration of between 5 wt % and 15 wt % and urea at a weight ratio of urea/HCl of from 0.7 to about 7, ii) providing solution B containing sodium hypochlorite (NaOCl) in an amount corresponding to a weight ratio of NaOCl to said HCl in said solution A of from about 1.0 to about 2.0; and iii) combining said solutions A and B to produce a biocidal composition having an acidic pH and containing active halogen of up to 25 wt %. A person skilled in the art of biocidal compositions might replace a part of hydrochloric acid in said solution A by other suitable acid, for example by phosphoric or sulfuric acid in a suitable concentration, preferably considering cheap technical grades, but in the most preferred embodiment of the invention, HCl is mainly used. A person skilled in the art of biocidal compositions might replace sodium hypochlorite in said solution B, partially or fully, by other suitable oxidant, for example by DC-DMH, DC-MEH, TCCA, Na-DCC, LiOCl, $Ca(OCl)_2$, $H_2O_2$, or peracetic acid in a suitable concentration, but in the most preferred embodiment of the invention, NaOCl is mainly used.

Without limiting themselves to any particular theory, the inventors believe that superior disinfection and anti-biofouling effects of the method of the invention, result not only from the combined activities of low pH and active halogen in killing the organisms, but also from chemical effects of acidic pH on the reactions between active chlorine and urea. It is noted that as far as the reagents are employed in accordance with the method of the invention, surprisingly effective antifouling results are achieved, regardless whether the reagents are incorporated into the system simultaneously or in any order, and regardless whether the reagents are premixed before injecting into the treated water system or incorporated separately.

EXAMPLES

Example 1

Chlorourea was prepared from aqueous NaOCl (12.9% wt % as Cl2), 32% HCl (wt %) and urea.

Solution A:

In a 100 ml flask, urea was dissolved (38.2 g) in 43.7 g H2O, followed by the addition of 18.1 g of 32% aqueous HCl (5.8 g HCl). The pH was 0.82.

Solution B:

An aqueous commercial NaOCl solution (12.9% wt % as Cl2, 11.3 g as Cl2) was provided, 87.5 g.

10 g of solution A and 8.8 g of solution B were added simultaneously during 10 min into a round bottom flask containing H2O (227 g) and equipped with a magnetic stir bar. Urea/HCl mass ratio was about 6.5; NaOCl/HCl mass ratio was about 2. A colorless solution was obtained, (pH 2.4), showing an absorption between 239-244 nm (UV).

Components A and B were added as two streams into water. Essentially in the application mode, two streams may be dozed directly to the treated water, one stream comprising urea hydrochloride and the other NaOCl.

Example 2

Chlorourea was prepared from aqueous NaOCl (12.9% wt % as Cl2), aqueous 32% HCl (wt %) and urea.

Solution A:

In a 100 ml flask, urea was dissolved (36 g, Mw 60, 600 mmol) in 41.2 g H2O, followed by the addition of 22.84 g of aqueous 32% HCl Wt % (7.31 g HCl, Mw 36.45, 200.5 mmol). The pH was 0.6.

Solution B:

An aqueous commercial NaOCl solution was provided, 110.1 g (12.9% as Cl2, Wt %, 14.2 g as Cl2, 200.1 mmol).

10 g of solution A and 11 g of solution B were added simultaneously during 5 min to a 500 ml round bottom flask containing H2O (286 g) and equipped with a magnetic stir bar. Urea/HCl mass ratio was about 5; NaOCl/HCl mass ratio was about 1.9. A clear solution was obtained (pH 2.5), showing an absorption at 239-242 nm (UV).

Components A and B were added as two streams into water. In the application mode, the two streams, one comprising urea hydrochloride and the other comprising NaOCl, may be dozed directly to the treated water.

Example 3

Biocidal experiments were performed, showing the efficacy of chlorourea in water with high TOC levels (up to 50 ppm) and in alginate beads experiment (a method simulating biofilm penetration).

Microbial Experiments Used the Following Materials

Inoculum of bacteria (Activated sludge taken from Domestic Waste Water treatment Plant—Haifa).

R2A agar for general counting.

Tryptone, in amounts of either 0.025, or 0.119 or 0.239 g solid tryptone, was weighed and dissolved in 1 liter of buffer.

Neutralization solution ($NaHSO_4$).

Titration solution, 7.84 g of sodium $Na_2S_2O_3 \cdot 5H_2O$ was dissolved in 1 liter distilled water.

Chlorourea solution, prepared from aq. urea hydrochloride (consisting of 5.8% HCl and 38.2% urea, Wt %) and a 12.9% aq NaOCl as $Cl_2$, Wt %); Urea, HCl:NaOCl 4:1:1 molar ratio.

Microbial Efficacy of Different Concentrations of the Chlorourea Solution Under Different TOC Loading The biocidal efficacy of the antifouling composition at different organic loads of 0, 10, 30 and 50 ppm TOC, was examined under different biocidal concentrations (2.5, 5 and 10 ppm) at pH 7.

1) 1 ml of inoculum was added to tryptone solutions (placed in 3 erlenmeyer flasks, 100 ml each, with different concentrations of TOC—0, 10, 30 and 50 ppm).

2) 1 ml of each sample was inoculated on R2A agar (pour plate method). The result stands for the bacteria count at zero time.

3) For each of the tryptone concentrations (0, 10, 30, 50 ppm TOC) an inoculum of bacteria (1 ml) and the appropriate biocide concentration were added.

4) After 30 and 60 min. of shaking (100 rpm), 1 ml of each sample was transferred to a tube filled with 9 ml of the neutralization solution. An aliquot of 1 ml was taken from this solution and added to another tube containing 9 ml of buffer solution. The solution was mixed under vortex. This operation was repeated 4 more times.

5) 1 ml from the two lowest dilutions was inoculated on a R2A agar (by the pour plate method).

6) After the plates were incubated at 25° C. for 5-7 days, the bacteria count was recorded. The results are presented in Table 1.

TABLE 1

% Kill of chlorourea (from urea/HCl/NaOCl 4:1:1 molar ratio). at different TOC concentrations after a contact time of 30 min.*

| | Biocide conc. (ppm as $Cl_2$) | | |
|---|---|---|---|
| TOC conc. (ppm) | 2.5 | 5 | 10 |
| 0 | 88.5 | 93.5 | 98.9 |
| 10 | 87.2 | 93.2 | 94.1 |
| 30 | 85.6 | 92.1 | 94.0 |
| 50 | 89.2 | 90.7 | 94.5 |

*After a contact time of 60 minutes, the results were similar

Other Biocides

Additional experiments were carried out to compare the activity of other biocides: Chlorourea (prepared from 46% Urea and 1.56% $Cl_2$, wt %, 35:1 molar ratio) and NaOCl. The results are given in Tables 2-3, respectively.

TABLE 2

% kill of Chlorourea (from Cl2 and urea) at different TOC concentrations after 30 min. contact time of (*)

| | Biocide conc. (ppm as $Cl_2$) | | |
|---|---|---|---|
| TOC conc. (ppm) | 2.5 | 5 | 10 |
| 0 | 82.5 | 88.2 | 90.1 |
| 10 | 76.3 | 83 | 84.3 |
| 30 | 75.3 | 85.5 | 90.4 |
| 50 | 74.8 | 85.1 | 88.2 |

(*)After a contact time of 60 minutes, the results were similar

TABLE 3

% kill of NaOCl at different TOC concentrations after 30 min. contact time

| | Biocide conc. (ppm as $Cl_2$) | | |
|---|---|---|---|
| TOC conc. (ppm) | 2.5 | 5 | 10 |
| 0 | 98.8 | 99.6 | 99.9 |
| 10 | 37.7 | 97.8 | 99.5 |
| 30 | 11.6 | 78.2 | 93.6 |
| 50 | 24.1 | 49.2 | 91.7 |

Microbial Efficacy of Different Concentrations of the Chlorourea Solution Under Different TOC Loading Against *Pseudomonas aeruginosa* (ATCC 15442)

The experiment shown above was repeated with *Pseudomonas aeruginosa* (ATCC 15442) instead of bacteria from activated sludge. This bacteria is abundant in biofilm structures and therefore could be an indicative bacteria for biofilm formation. The results are given in Tables 4-6.

TABLE 4

Efficacy of chlorourea (from urea.HCl—NaOCl 4:1:1 molar ratio) Against *Pseudomonas aeruginosa* (ATCC 15442) at different TOC concentrations after a contact time of 30 min.

| | % Kill Biocide conc. (ppm as $Cl_2$) | | |
|---|---|---|---|
| TOC conc. (ppm) | 2.5 | 5 | 10 |
| 0 | 96.0 | 100.0 | 100.0 |
| 10 | 91.7 | 99.8 | 100.0 |
| 30 | 84.8 | 98.7 | 100.0 |
| 50 | 80.5 | 97.8 | 100.0 |

TABLE 5

Efficacy of chlorourea (from urea.HCl—NaOCl 4:1:1 molar ratio) against *Pseudomonas aeruginosa* (ATCC 15442) at different TOC concentrationsafter 3 hrs contact time

| | % Kill Biocide conc. (ppm as $Cl_2$) | | |
|---|---|---|---|
| TOC conc. (ppm) | 2.5 | 5 | 10 |
| 0 | 100.0 | 100.0 | 100.0 |
| 10 | 100.0 | 100.0 | 100.0 |
| 30 | 100.0 | 100.0 | 100.0 |
| 50 | 100.0 | 100.0 | 100.0 |

TABLE 6

Efficacy of chlorourea (from urea.HCl—NaOCl 4:1:1 molar ratio) against *Pseudomonas aeruginosa* (ATCC 15442) at different TOC concentrations after 24 hrs contact time

| TOC conc. (ppm) | % Kill Biocide conc. (ppm as $Cl_2$) | | |
|---|---|---|---|
| | 2.5 | 5 | 10 |
| 0 | 100.0 | 100.0 | 100.0 |
| 10 | 100.0 | 100.0 | 100.0 |
| 30 | 100.0 | 100.0 | 100.0 |
| 50 | 100.0 | 100.0 | 100.0 |

Biocidal Activity Against Simulated Biofilm Systems

A biofilm simulation system developed by the Biofilm Bozeman Institute Montana (Grobe K. J., Zahler J., and Stewart P. S., 2002 in "Role of dose concentration in biocide efficacy against *Pseudomonas aeruginosa* Biofilms", J. Industrial Microbiology & Biotechnology, vol. 29, pp 10-15), was used in this experiment to evaluate the efficacy of chlorourea against biofilm.

Preparation of the Alginate Beads

The biofilm simulation was created by entrapping bacteria in alginate gel beads. A plate of R2A agar was streaked with *Pseudomonas aeruginosa* (ATCC 15442) and incubated at 35° C. overnight. Buffer phosphate at pH 7.2 was used to scrap off the bacteria from the agar plate and to create a suspension. The bacterial suspension was mixed with an equal volume of an aqueous 4% sodium alginate solution, to make a final 2% alginate solution. The alginate and bacterial slurry were placed in a 50 ml syringe attached to a 22 gauge needle, connected to a compressed air tank, allowing the syringe to be pressurized. At 20 psig pressure a stream of small drops was forced out and dropped into a stirred solution of 50 mM $CaCl_2$. The $Ca^{+2}$ cross linked the alginate, and semi solid beads with entrapped bacterial cells were formed. The beads were allowed to stir in the $CaCl_2$ solution for about 20 minutes, and then rinsed in a dilute 5 mM $CaCl_2$ solution. Several flasks containing 100 beads each were incubated overnight at 35° C. on a rotating shaker in a buffer solution (at pH 7) with 5 mM addition of $CaCl_2$ to maintain the beads structure. The resulting beads diameter is about 2 mm.

General Description of the Experiment

At the beginning of the experiment, the supernatant of the beads buffer suspension containing 5 mM $CaCl_2$ was decanted and replaced by the 100 ml biocide solution with the required concentration. Urea-chlorine compositions were prepared by dissolving urea 15.02 g (250.3 mmol, 15% concentration) and 1.17 g $Br_2$ (7.32 mmol, 1.17% concentration) in 84 g $H_2O$ (34.2:1 urea:$Br_2$ molar ratio). After different interval contact times, 10 beads were removed and placed in a 5 g/l sodium thiosulfate solution containing 50 mM sodium citrate. The sodium citrate was used to dissolve the alginate gel and release the bacteria into the solution. The neutralizer-citrate solution was placed in the refrigerator for 2 hours, than diluted and placed on R2A agar plates using pour plate technique. The plates were incubated at 35° C. for 24-48 hours and counted. The efficacy and toxicity of the neutralizer were checked as well as a control experiment without biocide addition. Four concentrations (0.5, 1, 2.5 and 5 ppm) were tested at four different contact times (5, 15, 30, and 60 min). Table 7 describes the surviving colony forming units (CFU) of the bacteria after the biocide treatment at different contact times.

TABLE 7

Biocidal efficacy of a chlorourea (prepared from 46% Urea and 1.56% Cl2, wt %, 35:1 molar ratio) against bacterial beads survival of bacteria (CFU) as a function of biocide loading and contact time.

| Contact Time | Biocide concentration (ppm as $Cl_2$) | | | |
|---|---|---|---|---|
| | 0.5 | 1 | 2.5 | 5 |
| 0 | 7.10E+06 | 7.10E+06 | 7.10E+06 | 7.10E+06 |
| 5 | 6.90E+06 | 5.10E+06 | 6.60E+06 | 5.35E+06 |
| 15 | 5.70E+06 | 6.60E+06 | 1.30E+06 | 5.90E+04 |
| 30 | 6.10E+06 | 2.60E+06 | 8.10E+03 | 4.00E+01 |
| 60 | 4.70E+06 | 3.75E+04 | 1.00E+00 | 1.00E+00 |

The bacterial concentration count was reduced by 0.2 logs at a biocide concentration of 0.5 ppm, and by 2 logs at a biocide concentration of 1 ppm, after 60 minutes of contact time. After the same contact time, 6.9 logs of the bacterial counts were reduced (100% kill), with the 2.5 and 5 ppm concentrations (as $Cl_2$), after 60 minutes.

Long Contact Time

Additional experiments were carried out to compare the activity of chlorourea (from urea and $Cl_2$) and of NaOCl against bacterial beads after a long contact time of 24 hours. The results are given in Tables 8 and 9.

TABLE 8

Biocidal efficacy of chlorourea (from urea and Cl2) after 24 hours contact time against bacterial beads survival of bacteria (CFU) as a function of biocide loading.

| Contact Time | Biocide concentration (ppm as $Cl_2$) | | | |
|---|---|---|---|---|
| | 0.5 | 1 | 2.5 | 5 |
| 0 | 1.40E+07 | 1.40E+07 | 1.40E+07 | 1.40E+07 |
| 24 hours | 1.00E+00 | 1.00E+00 | 1.00E+00 | 1.00E+00 |

TABLE 9

Biocidal efficacy of NaOCl against bacterial beads survival of bacteria (CFU) as a function of biocide loading, after a contact time of 24 hours.

| Contact Time | Biocide concentration (ppm as $Cl_2$) | | | |
|---|---|---|---|---|
| | 0.5 | 1 | 2.5 | 5 |
| 0 | 1.40E+07 | 1.40E+07 | 1.40E+07 | 1.40E+07 |
| 24 hours | 3.6E+06 | 2.53E+06 | 1.00E+00 | 1.00E+00 |

While the invention has been described using some specific examples, many modifications and variations are possible. It is therefore understood that the invention is not intended to be limited in any way, other than by the scope of the appended claims.

The invention claimed is:
1. A method for manufacturing a biocidal and antifouling composition in an aqueous mixture, comprising the steps of i) providing aqueous solution A containing HCl at a concentration of between 5 wt % and 15 wt %, and urea at a weight ratio of urea/HCl of from 0.7 to 7;
ii) providing aqueous solution B comprising NaOCl; and
iii) combining said aqueous solutions A and B;
wherein said solutions A and B are combined, optionally with an amount of additional water, in such a ratio of volumes so as to provide a pH lower than 6.0.

2. The method for manufacturing a biocidal composition in an aqueous mixture according to claim 1, comprising the steps of
i) providing aqueous solution A containing HCl at a concentration of between 5 wt % and 15 wt %, and urea at a weight ratio of urea/HCl of from 0.7 to 7;
ii) providing aqueous solution B containing sodium hypochlorite (NaOCl) in an amount corresponding to a weight ratio of NaOCl to said HCl in said solution A of from 1.0 to 2.0; and
iii) providing said aqueous mixture by combining a quantity of said aqueous solutions A and B with an amount of additional water;
wherein said solutions A and B create an acidic pH in said aqueous mixture and active chlorine in a concentration of less than 25 wt % (as $Cl_2$).

3. The method according to claim 2, wherein said amount of additional water in said step iii) is not higher than said quantity of solutions A and B, said aqueous mixture containing active chlorine in a concentration of between 1 and 20 wt %.

4. The method according to claim 3, wherein said aqueous mixture is employed as a stock solution and is admixed into industrial or agricultural water needing anti-fouling treatment.

5. The method according to claim 2, wherein said amount of additional water in said step iii) is higher than said quantity of solutions A and B, said aqueous mixture containing active chlorine in a concentration of 20 ppm or less.

6. The method according to claim 5, wherein said solutions A and B are injected into a tank or into a circuit comprising industrial or agricultural water needing disinfection and/or anti-fouling treatment.

7. The method according to claim 2, wherein said aqueous mixture comprises a water bulk or a water stream, and wherein said combining solutions A and B comprises their mixing or their addition to said aqueous mixture in any order.

8. The method of manufacturing a biocidal composition in an aqueous mixture according to claim 2, comprising steps of
i) admixing solution A into said aqueous mixture, wherein said solution A contains HCl at a concentration of between 5 wt % and 15 wt % and urea at a weight ratio of urea/HCl of from 0.7 to 7; and
ii) admixing solution B into said aqueous mixture, wherein said solution B contains sodium hypochlorite (NaOCl) in an amount corresponding to a weight ratio of NaOCl to said HCl in said solution A of from 1.0 to 2.0;
thereby creating a pH of 3.0 or less in said aqueous mixture and active chlorine at a concentration of less than 25 wt % (as $Cl_2$).

9. The method according to claim 8, comprising admixing hydrochloric acid into water or into an aqueous mixture of urea, wherein said hydrochloric acid is added as a gas or as a water solution.

10. The method according to claim 8, comprising admixing urea into water or into an aqueous solution of HCl, wherein said urea is added as a solid or as a water solution.

11. The method according to claim 8, comprising admixing NaOCl into a water solution comprising HCl and urea, wherein said NaOCl is added as an alkali water solution.

12. The method according to claim 8, wherein said urea/HCl ratio is between 1.5 and 6.0.

13. The method according to claim 8, comprising
i) admixing solution A into an aqueous mixture, wherein said solution A contains HCl between 10 wt % and 15 wt % and urea at a weight ratio of urea/HCl of between 0.7 and 7, thereby obtaining a solution having a pH of 0.0 or less; and
ii) admixing solution B into said aqueous mixture, wherein said solution B contains sodium hypochlorite (NaOCl) in an amount corresponding to a weight ratio of NaOCl to HCl in said solution A of between 1.0 and 2.0;
thereby creating active chlorine of less than 12.5 wt % (as $Cl_2$) and a pH of 3.0 or less.

14. The method according to claim 8, comprising combining at least two liquid streams, one of which comprises said solution A and the other said solution B.

15. The method according to claim 8, comprising combining at least two liquid streams, one of which comprises aqueous solution of HCl and urea, and the other aqueous solution of NaOCl.

16. An aqueous biocidal composition comprising a mixture of hydrochloric acid (HCl), urea, and sodium hypochlorite (NaOCl), wherein said HCl is added to the mixture as a solution of a concentration of between 5 wt % and 15 wt %, urea is added as a solution having a weight ratio of urea/HCl of between 0.7 and 7; and NaOCl is added to an amount corresponding to a weight ratio of NaOCl/HCl of between 1.0 and 2.0.

17. The biocidal composition according to claim 16, comprising active chlorine at a concentration of less than 25 wt %.

18. The biocidal composition according to claim 16, having a pH of 3.0 or less.

19. The biocidal composition according to claim 16, acting synergistically against biofouling agents by means of active halogen and high acidity, having an active chlorine less than 12.5 wt % and acidic pH.

20. The biocidal composition according to claim 16, acting as a biofouling agent by means of active halogen in an acidic pH, wherein said halogen is active chlorine at a concentration higher than 0.1 ppm.

21. The method according to claim 1, wherein said aqueous mixture comprises industrial waters selected from cooling water, production water, water for agricultural use, water in paper mill process, effluent water, or waste water.

22. A biocidal composition comprising two aqueous solutions, A and B,
the aqueous solution A contains HCl at a concentration of between 5 wt % and 15 wt % and urea at a weight ratio of urea/HCl of from 0.7 to about 7, and
the aqueous solution B contains sodium hypochlorite (NaOCl) in an amount corresponding to a weight ratio of NaOCl to said HCl in said solution A of from about 1.0 to about 2.0.

23. The composition according to claim 22, wherein said solutions are combined to produce a biocidal composition having an acidic pH and containing an active halogen of less than 25 wt %.

24. The composition according to claim 22, wherein said solutions are combined before or after contacting industrial waters.

25. The composition according to claim 22, wherein said solutions are diluted with water before being combined.

* * * * *